United States Patent
Yang (10) Patent No.: US 12,370,303 B2
(45) Date of Patent: *Jul. 29, 2025

(54) PATCH-TYPE DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 774 days.

This patent is subject to a terminal disclaimer.

(21) Appl. No.: 17/615,109

(22) PCT Filed: Dec. 31, 2019

(86) PCT No.: PCT/CN2019/130445
§ 371 (c)(1),
(2) Date: Nov. 30, 2021

(87) PCT Pub. No.: WO2021/017408
PCT Pub. Date: Feb. 4, 2021

(65) Prior Publication Data
US 2022/0218899 A1   Jul. 14, 2022

(30) Foreign Application Priority Data

Aug. 1, 2019   (WO) ................ PCT/CN2019/098784

(51) Int. Cl.
*A61M 5/142*   (2006.01)
*A61B 5/145*   (2006.01)
(Continued)

(52) U.S. Cl.
CPC ..... *A61M 5/14236* (2013.01); *A61B 5/14532* (2013.01); *A61M 5/14216* (2013.01);
(Continued)

(58) Field of Classification Search
CPC .......... A61M 5/14216; A61M 5/31583; A61M 2005/14506; A61M 5/31538;
(Continued)

(56) References Cited

U.S. PATENT DOCUMENTS 6,446,627 B1 * 9/2002 Bowman ............... G06M 1/083
128/200.23
2003/0199824 A1 * 10/2003 Mahoney ............ A61M 5/1452
604/155
(Continued)

FOREIGN PATENT DOCUMENTS

CN   101208515      6/2008
CN   101208515 A *  6/2008   ........ A61M 5/14244
(Continued)

OTHER PUBLICATIONS

Yang, Cuijun, Administration system containing position detection unit, Nov. 23, 2016, Machine Translation of the Description of CN 106139311 A (Year: 2016).*
(Continued)

*Primary Examiner* — William R Carpenter
*Assistant Examiner* — Robert F Allen
(74) *Attorney, Agent, or Firm* — JCIP GLOBAL INC.

(57) ABSTRACT

A patch-type drug infusion device includes an infusion unit. The infusion unit includes a drug storage unit, a piston, a rigid screw, a rotating shaft, a rotatable driving unit, a driving wheel provided with wheel teeth, a power unit and a rebound unit. The driving unit can rotate around the rotating shaft, driving the driving portion of the driving unit to push the wheel teeth to rotate the driving wheel which engages the rigid screw to move forward in a non-rotating way. The device also includes position detectors, a program unit, an infusion needle and an adhesive patch. The program unit is connected to the infusion unit to control drug infusion (Continued)

and convert received electrical or magnetic signals into the piston position information.

6 Claims, 7 Drawing Sheets (51) Int. Cl.
    *A61M 5/145* (2006.01)
    *A61M 5/168* (2006.01)
    *A61M 5/315* (2006.01)
    *G16H 20/17* (2018.01)
    *G16H 40/67* (2018.01)
    *A61M 5/172* (2006.01)

(52) U.S. Cl.
    CPC ...... *A61M 5/14248* (2013.01); *A61M 5/1452* (2013.01); *A61M 5/1454* (2013.01); *A61M 5/16877* (2013.01); *A61M 5/31583* (2013.01); *G16H 20/17* (2018.01); *G16H 40/67* (2018.01); *A61M 2005/14208* (2013.01); *A61M 2005/14252* (2013.01); *A61M 2005/14506* (2013.01); *A61M 5/1723* (2013.01); *A61M 2205/0233* (2013.01); *A61M 2205/3317* (2013.01); *A61M 2205/3327* (2013.01); *A61M 2230/201* (2013.01)

(58) Field of Classification Search
    CPC ........ A61M 2205/10; A61M 2205/106; A61M 2005/14533; A61M 2005/14208; A61M 5/16804; A61M 5/16877; A61M 5/1454; A61M 5/1452; A61M 5/14236
    See application file for complete search history.

(56) References Cited

U.S. PATENT DOCUMENTS

| | | | | |
|---|---|---|---|---|
| 2003/0236498 | A1* | 12/2003 | Gross | A61M 5/14216 604/141 |
| 2005/0238507 | A1* | 10/2005 | Dilanni | F04B 9/08 417/415 |
| 2008/0051727 | A1* | 2/2008 | Moberg | A61M 5/14248 604/207 |
| 2010/0078490 | A1* | 4/2010 | Fenlon | A61M 15/009 116/284 |
| 2012/0165734 | A1* | 6/2012 | Auld | A61M 5/16877 604/151 |
| 2016/0144101 | A1* | 5/2016 | Pananen | A61M 5/1452 604/152 |
| 2018/0126068 | A1* | 5/2018 | Nazzaro | A61M 5/1452 |
| 2019/0117881 | A1* | 4/2019 | Yang | A61M 5/16804 |
| 2022/0143304 | A1* | 5/2022 | Yang | A61M 5/1684 |
| 2022/0193339 | A1* | 6/2022 | Yang | A61M 5/1454 |
| 2022/0233774 | A1* | 7/2022 | Yang | G16H 20/17 |
| 2022/0295896 | A1* | 9/2022 | Connelly | A24F 40/51 |
| 2022/0305201 | A1* | 9/2022 | Yang | G16H 40/63 |
| 2023/0173174 | A1* | 6/2023 | Yang | A61M 5/172 604/65 |

FOREIGN PATENT DOCUMENTS

| | | | | |
|---|---|---|---|---|
| CN | 102711898 | | 10/2012 | |
| CN | 102711898 A | * | 10/2012 | ........... A61B 5/1451 |
| CN | 103260678 | | 8/2013 | |
| CN | 103260678 A | * | 8/2013 | ............ A61F 9/007 |
| CN | 103463695 A | * | 12/2013 | |
| CN | 106139311 | | 11/2016 | |
| CN | 106139311 A | * | 11/2016 | |
| WO | 2006105793 | | 10/2006 | |
| WO | WO-2006105793 A1 | * | 10/2006 | ........ A61M 5/14244 |
| WO | WO-2019129618 A1 | * | 7/2019 | .......... A61M 5/3157 |

OTHER PUBLICATIONS

"International Search Report (Form PCT/ISA/210) of PCT/CN2019/130445," mailed on Apr. 27, 2020, with English translation thereof, pp. 1-5.

"Search Report of Europe Counterpart Application", issued on Jul. 28, 2023, pp. 1-8.

* cited by examiner

PATCH-TYPE DRUG INFUSION DEVICE

CROSS-REFERENCE TO RELATED APPLICATION

This application is a 371 of international application of PCT application serial no. PCT/CN2019/130445 filed on Dec. 31, 2019, which claims the priority benefit of PCT application serial no. PCT/CN2019/098784 filed on Aug. 1, 2019. The entirety of each of the above mentioned patent applications is hereby incorporated by reference herein and made a part of this specification.

TECHNICAL FIELD

The present invention mainly relates to the field of medical instruments, in particular to a patch-type drug infusion device.

BACKGROUND

A drug infusion device can continuously deliver drug into a patient's body for disease treatment. Drug infusion devices are widely used in the field of diabetes treatment, which continuously infuse required dosage of insulin into the patient's subcutaneous tissue, thereby simulating the secretion function of the pancreas to keep the blood glucose stable. The drug fluid is usually stored inside the infusion pump. The existing drug infusion device, controlled by remote device, is usually attached directly on the patient's skin through a medical adhesive tape.

At present, the existing drug infusion devices are relatively large in size, and are prone to be caught by clothes after sticking to the skin. So the user experience is poor. At the same time, the internal structure is complex, with higher design and production costs.

Therefore, the prior art desperately needs a drug infusion device with smaller size and lower cost.

BRIEF SUMMARY OF THE INVENTION

The embodiment of this invention discloses a patch-type drug infusion device. By adjusting the internal structure and layout of the infusion device, the volume of the infusion device and the production cost are both reduced.

This invention discloses a patch-type drug infusion device, which includes an infusion unit, the infusion unit comprises drug storage unit(s), piston(s) and rigid screw(s), the piston is arranged in the drug storage unit; metal piece, fixedly connected to a rigid screw, is arranged on the piston; rotating shaft, rotatable driving unit(s) and driving wheel(s) provided with wheel teeth, the driving unit includes one driving portion, and the driving unit can rotate around the rotating shaft, driving the driving portion to push the wheel teeth to rotate the driving wheel which engages the rigid screw to move forward in a non-rotating way; and power unit(s) and rebound unit(s), the power unit and the rebound unit apply force to the driving unit respectively to make the driving unit rotate reciprocally; position detector(s), the metal piece and the position detector interact to generate electrical or magnetic signals; program unit, the program unit is connected to the infusion unit to control drug infusion and convert received electrical or magnetic signals into piston position information; infusion needle, one end of the infusion needle is connected to the outlet of the drug storage unit, while the other end pierces the skin to achieve drug infusion; and adhesive patch, the adhesive patch can attach the infusion unit or the program unit to the skin surface.

According to one aspect of the present invention, the rigid screw is a metal screw, and the metal piece is electrically connected with the metal screw, so that the metal piece and the corresponding position detector constitute a capacitor, and the linear movement of the metal piece causes a change in capacitance making the corresponding position detector generate an electrical signal.

According to one aspect of the present invention, the metal piece is a magnetic metal piece, and the position detector is magnetic induction detector, the linear movement of the magnetic metal piece causes a change in the magnetic field around each position detector making each position detector generate a magnetic signal.

According to one aspect of the present invention, the direction in which the power unit applies a force to the driving unit is parallel to the forward direction of the rigid screw.

According to one aspect of the present invention, it also includes two driving units and one driving wheel, the two driving units are coaxial, or the two driving units are respectively disposed on the two sides of the driving wheel.

According to one aspect of the present invention, it further includes a clutch structure movably disposed on the driving wheel, the rigid screw passes through the clutch structure, and the clutch structure is provided with an internal thread that cooperates with the rigid screw, the driving wheel drives the clutch structure to rotate which, with the internal thread, engages the rigid screw to move forward in a non-rotating way.

According to one aspect of the present invention, it further comprises blocking wall(s), and the driving unit stops rotating upon contacting the blocking wall.

Compared with the prior art, the technical solution of the present invention has the following advantages:

In the patch-type drug infusion device disclosed in the present invention, the driving unit includes one driving portion, and the driving unit rotates to drive the driving portion to push the wheel teeth to rotate the driving wheel. Disposing one driving portion on the driving unit reduces the overall width of the driving unit and the driving unit's rotation amplitude, so that the internal structure of the infusion device will be more compact, leading to reduced volume of the infusion device and lower production cost. Secondly, the rigid screw moves in a linear non-rotating manner, which simplifies the design, manufacturing and position detection of the piston and reduces design and production costs.

Furthermore, the direction in which the power unit applies a force to the driving unit is parallel to the forward direction of the rigid screw. Such a design can make full use of the internal structural layout of the infusion device, reduce the space required for mechanical operation of the power unit, and thereby reduce the volume of the infusion device.

Furthermore, the infusion device includes two driving units and one driving wheel, the two driving units are coaxial, or the two driving units are respectively disposed on the two sides of the driving wheel. The two driving units and one driving wheel cooperate with each other, which reduces the rotation amplitude of the driving unit, making the internal structure of the infusion device more compact, and further reducing the volume of the infusion device. At the same time, the two driving units cooperating with each other can improve the infusion accuracy of the device, so that the amount of infused drugs can be controlled precisely.

DETAILED DESCRIPTION

As described above, the structure of the internal driving unit of the prior art infusion device is complicated, resulting in an increase in the volume and production cost of infusion device.

It is found through research that the above-mentioned problems are caused by the larger width and rotation amplitude of the driving unit, the more driving wheels with the larger distance between the driving wheels, which increases the assembly space of the internal structure of the infusion device.

In order to solve this problem, the present invention provides a patch-type drug infusion device. The internal structure of the patch is more compact, and the design is simpler, reducing the volume of the device and the production cost.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in following description of the drawings.

The First Embodiment

Figure 1A:
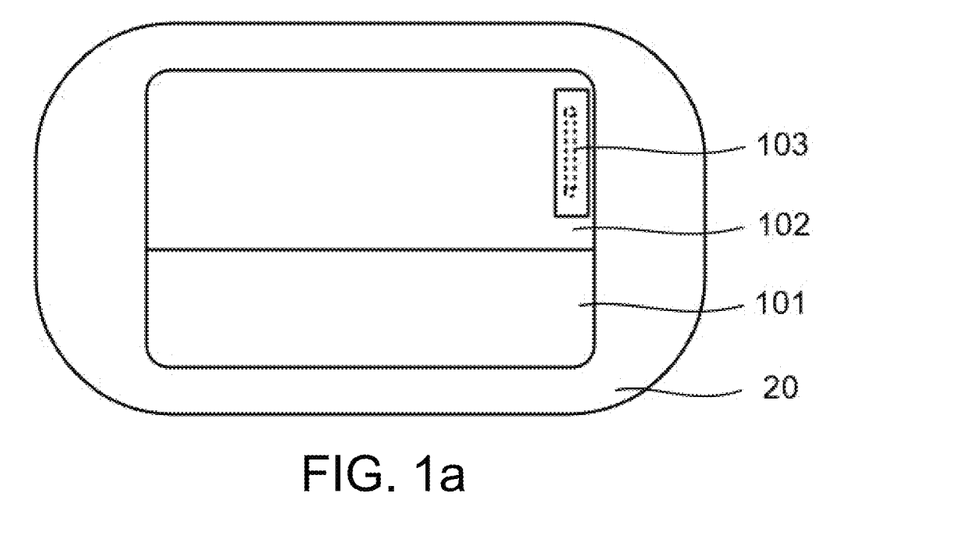
FIG. 1a-FIG. 1b are schematic top plan views of two patch drug infusion devices according to one embodiment of the present invention.
Figure 1B:
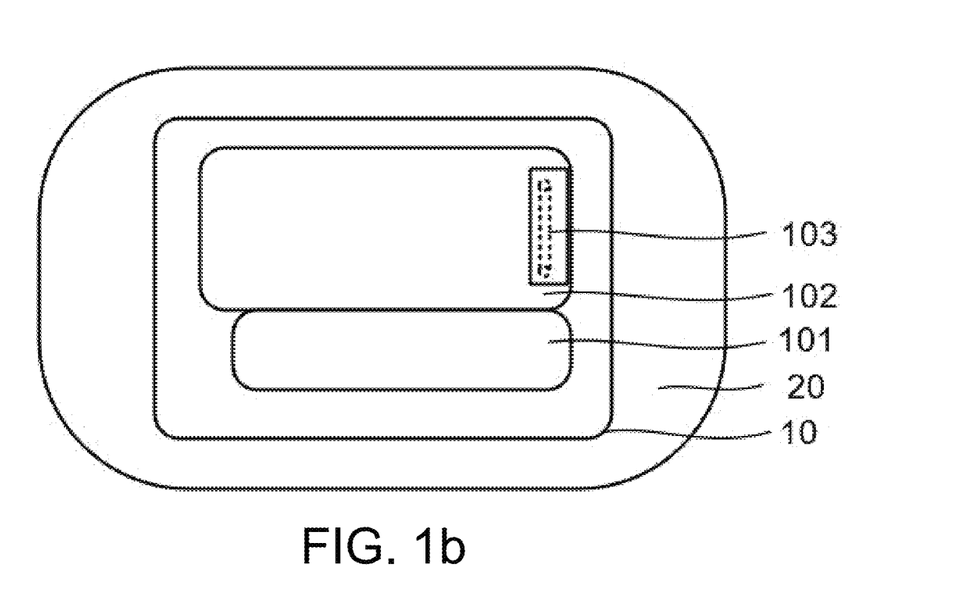

FIG. 1a and FIG. 1b are schematic top structural diagrams of a patch-type drug infusion device according to one embodiment of the present invention.

The patch-type drug infusion device includes an adhesive patch 20, program unit 101, infusion unit 102 and infusion needle 103.

The program unit 101 is used for controlling drug infusion, controlling power output of the power unit, receiving signals from position detector(s), establishing wireless communication with remote devices, and the like.

The infusion unit 102 includes various units for realizing the mechanical function for drug infusion, which will be described in detail below.

In the embodiment of the present invention, the program unit 101 and the infusion unit 102 are designed separately and connected by a waterproof plug. The program unit 101 can be reused, while the infusion unit 102 can be discarded after a single use. In another embodiment of the present invention, the infusion unit 102 and the program unit 101 are disposed inside the same housing 10 and connected by a wire, which both units will be discarded together after a single use, as shown in FIG. 1b.

The adhesive patch 20 is used to attach the infusion unit 102 or the program unit 101, or both of them to the skin surface as a whole.

One end of the infusion needle 103 is connected to the outlet of the drug storage unit, while the other end pierces the skin to infuse the drug subcutaneously. In the embodiment of the present invention, the infusion needle 103 is disposed at one end of the infusion unit 102. In other embodiments of the present invention, the infusion needle 103 may be disposed at other positions according to its functions or structural features of the device, such as being disposed at the middle portion of the device, which is not specifically limited herein. The infusion needle 103 is a rigid infusion needle or a flexible infusion needle, or designed according to its different positions and functions, the design of infusion needle 103 can also adopt a combination of rigid infusion needle(s) and flexible infusion needle(s), which is not specifically limited herein. Preferably, in the embodiment of the present invention, the infusion needle 103 is a rigid infusion needle.

Figure 2:
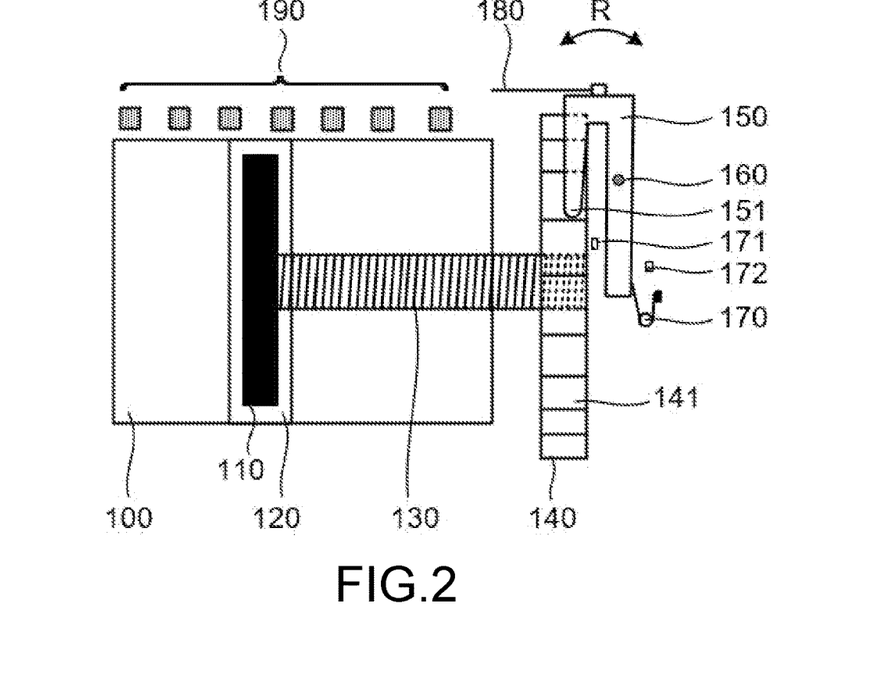
FIG. 2 is a schematic diagram of the main structure of an infusion unit according to one embodiment of the present invention.
Figure 3:
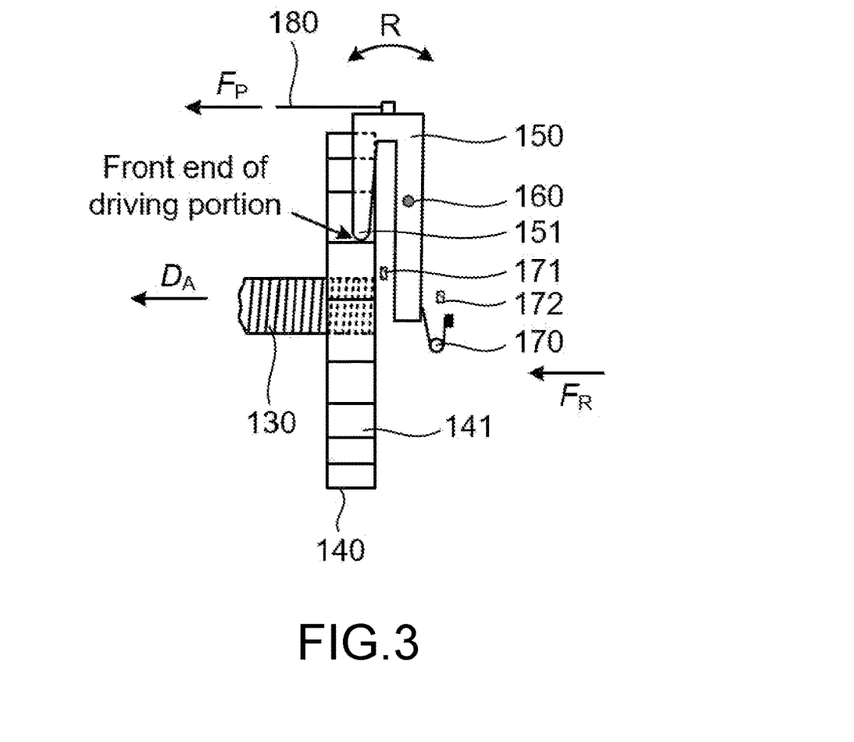
FIG. 3 is a schematic structural diagram of cooperation between a driving unit and a driving wheel according to another embodiment of the present invention.

Please refer to FIG. 2-FIG. 3. FIG. 2 is a schematic main structural diagram of an infusion unit 102 of a patch-type drug infusion device according to an embodiment of the present invention. FIG. 3 is a schematic structural diagram of the driving portion 151 in FIG. 2, pushing the wheel teeth 141.

The internal structure of the infusion unit 102 mainly includes the drug storage unit 100, the piston 120, the rigid screw 130, the driving wheel 140, the driving unit 150, the rotating shaft 160, the rebound unit 170 and the power unit 180.

The drug storage unit 100 is used for storing liquid drug. Drugs include, but are not limited to, insulin, glucagon, antibiotics, nutrient solutions, analgesics, morphine, anticoagulants, gene therapy drugs, cardiovascular drugs or chemotherapy drugs, etc.

The piston 120 is used to infuse liquid drug into the body.

The rigid screw 130 is connected to the piston 120 and the driving wheel 140, respectively. In the embodiment of the present invention, the driving wheel 140 advances the rigid screw 130 forward by screwing, the rigid screw 130 then forces the piston 120, arranged in the drug storage unit 100, to move forward, so as to achieve the purpose of drug infusion.

The peripheral surface of the driving wheel 140 is provided with wheel teeth 141. The wheel teeth 141 are gear teeth or ratchet teeth. Specifically, in the embodiment of the present invention, for improving driving efficiency, the wheel teeth 141 are ratchet teeth which can be pushed more easily.

One driving portion 151 is provided at one end of the driving unit 150 to push the wheel teeth 141 and thereby rotate the driving wheel 140. The driving unit 150 is movably connected to the rotating shaft 160, and is also connected with the power unit 180 and the rebound unit 170, respectively. The power unit 180 and the rebound unit 170 cooperate with each other to make the driving unit 150 rotate reciprocally around the rotating shaft 160, as shown in the R direction in FIG. 3. When the driving unit 150 performs one reciprocal rotation, the driving wheel 140 drives the rigid screw 130 forward by one step, and the rigid screw 130 engages the piston 120 to infuse one unit of drug.

In the embodiment of the present invention, the rebound unit 170 is a spring. In other embodiments of the present invention, the rebound unit 170 can also be an elastic piece, an elastic plate, an elastic rod, etc. The type and material selection of the rebound unit 170 are not specifically limited herein, as long as it can satisfy the condition of making the driving unit 150 rotate in the return direction.

The power unit 180 is a linear actuator. In the embodiment of the present invention, the power unit 180 is an electrically driven linear actuator or an electrically heated linear actuator. By alternately turning on and off, the power unit 180 outputs power in pulses. In other embodiments of the present invention, the power unit 180 may be other types, eg. mini-airbag.

In the embodiment of the present invention, when the power unit 180 pulls the driving unit 150 by force $F_P$, the driving unit 150 rotates counter-clockwise around the rotating shaft 160, driving the driving portion 151 to push the wheel teeth 141 forward, and thereby making the driving wheel 140 rotate. The driving wheel 140 then moves the rigid screw 130 forward in the $D_A$ direction. At this time, the rebound unit 170 builds a gradually increasing elastic force $F_R$. When the power unit 180 stops applying force and under the action of only the elastic force $F_R$, the driving unit 150 will rotate clockwise around the rotating shaft 160. At this time, the driving portion 151 stops pushing the wheel tooth 141, but just slides on the surface of the adjacent wheel tooth 141 until it slides to the next driving position, and the driving wheel 140 stop rotating. The driving unit 150 completes one reciprocal rotation.

It should be noted here that in order to minimize the impact of manufacturing tolerances and ensure that the wheel teeth 141 can be pushed during each reciprocal rotation for infusion safety, after the driving portion 151 slides to the next driving position, the driving unit 150 can be further rotated clockwise by an appropriate distance to move the driving portion 151 slightly away from the driving position.

Preferably, in the embodiment of the present invention, the direction of $F_P$, the direction of F and the direction of $D_A$ are parallel to one another. This parallel design can make full use of space and optimize the structural relationships inside the infusion device, making the internal structure more compact. In other embodiments of the present invention, the $F_P$ direction and the $F_R$ direction may not be parallel, which is not specifically limited herein, as long as the purpose of making the driving unit 150 reciprocate can be achieved.

In the embodiment of the present invention, blocking walls 171 and 172 that can stop the driving unit 150 from rotating are also provided. And an electrical signal may be triggered when the driving unit 150 contacts the blocking wall 171 or 172, allowing the program unit 101 to control the power output of the power unit 180. In another embodiment of the present invention, only the blocking wall 171 or only the blocking wall 172 may be provided, so that the driving unit 150 can stop rotating in either direction. Blocking wall(s) in combination with a time controller allow the program unit 101 to control the power output of the power unit 180. In another embodiment of the present invention, no blocking wall is provided, and the rotation of the driving unit 150 is completely controlled by a time controller in the program unit 101.

It should be noted that, the position of the blocking wall 171 or 172 is not specifically limited in the embodiment of the present invention, as long as the condition that the driving unit 150 stops rotating can be satisfied.

Figure 4A:
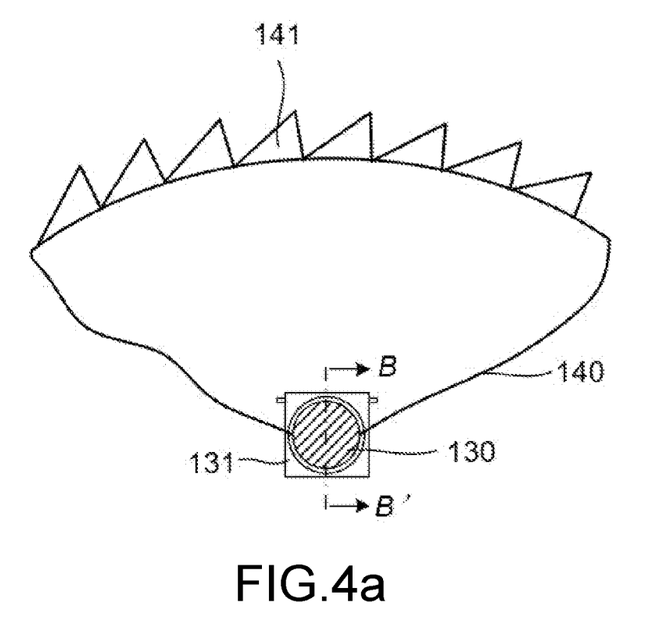
FIG. 4a-FIG. 4b are schematic diagrams of the clutch structure under different perspectives according to one embodiment of the present invention.
Figure 4B:
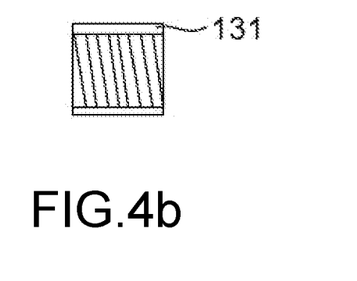

FIG. 4a-FIG. 4b are schematic structural diagrams of a clutch structure 131 according to an embodiment of the present invention. FIG. 4b is a schematic cross-sectional view of the clutch structure 131 taken along the line B-B' in FIG. 4a.

The embodiment of the present invention further includes a clutch structure 131. The clutch structure 131 is disposed at the central position of the driving wheel 140, and the rigid screw 130 passes through the clutch structure 131. The clutch structure 131 is provided with an internal thread matching the external thread of the rigid screw 130, as shown in FIG. 4b. During drug infusion, the driving wheel 140 drives the clutch structure to rotate synchronously, and the clutch structure advances the rigid screw 130 forward through the internal thread. Obviously, in the embodiment of the present invention, the rigid screw 130 only advances in its own axial direction without rotating. In another embodiment of the present invention, the driving wheel 140 has an internal thread, which can directly cooperate with the external thread of the rigid screw 130.

Figure 5:
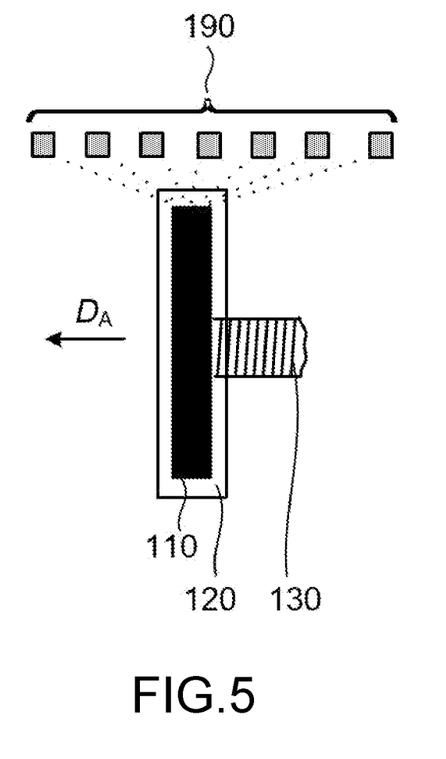
FIG. 5 is a schematic structural diagram of a piston and a position detector according to one embodiment of the present invention.

FIG. 5 is a schematic structural diagram of a metal piece 110 and a position detector 190 according to an embodiment of the present invention.

The infusion device according to the embodiment of the present invention further includes one or more position detectors 190. The position detector 190 interacts with the metal piece 110 to detect the position of the metal piece 110, and thereby determine the position of the piston 120 to calculate the remaining amount of drug in the drug storage unit 100. Specifically, in the embodiment of the present invention, the metal piece 110 is a magnetic metal piece, and the position detector 190 is magnetic position detector. When the metal piece 110 is located at a certain position, the location of every position detector 190 has a certain magnetic field size and direction, allowing the position of the piston 120 to be accurately detected. When the piston 120 is moving, the magnitude and direction of the magnetic field at the location of every position detector 190 changes accordingly, in which way the position of the piston 120 is detected in real time. The position detector 190 sends magnetic signal(s) or magnetic signal change to the program unit 101. After processed, the signal is converted into position information of the piston 120, which is then used to calculate the remaining drug amount.

According to the specifications of the drug storage unit 100, the number of the position detectors 190 can be one, two or more. Specifically, in the embodiment of the present invention, the number of the position detectors 190 is seven. In another embodiment of the present invention, the number of the position detectors 190 is two. In still another embodiment of the present invention, only one position detector 190 is provided.

It should be noted that when there are more than two position detectors 190, preferably, the position detectors 190 are linearly and equally spaced. The position detector 190 can be disposed in the infusion unit 102, or at a position, corresponding to the changing position of the piston 120, in the program unit 101, or embedded in the side wall of the drug storage unit 100, or located on the inner surface of the drug storage unit 100. The position detectors 190 may also be arranged in other ways, which are not specifically limited herein, as long as the conditions for detecting the position of the piston 120 can be satisfied.

As previously mentioned, the rigid screw 130 only moves along its own axial direction without rotating. Therefore, the metal piece 110, embedded in the piston 120 and fixedly connected to the rigid screw 130, can also be advanced non-rotating only along the axial direction of the rigid screw 130. Compared with detecting position with a rotating screw, the embodiment of the present invention only detects magnetic field signal(s) in one-dimensional axial direction or two-dimensional plane (determined by the moving direction of the screw and a detector). The detecting principle, the operation and structural design are much simpler, and the position information is more accurate, reducing the cost of design and production.

The Second Embodiment

Figure 6A:
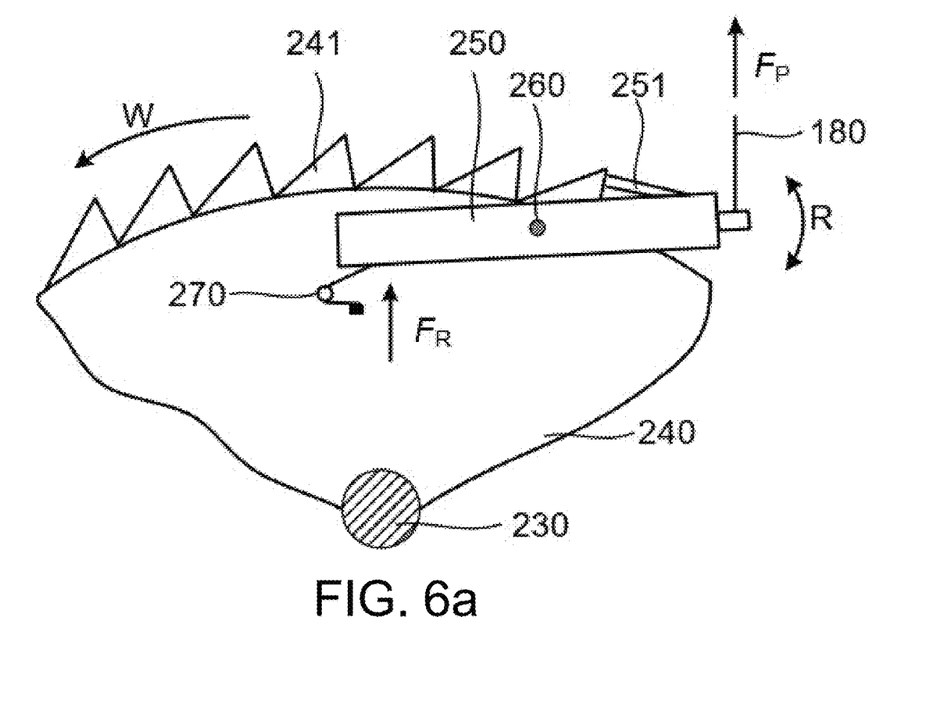
FIG. 6a-FIG. 6b are schematic structural diagrams of cooperation between a driving unit and a driving wheel according to another embodiment of the present invention.
Figure 6B:
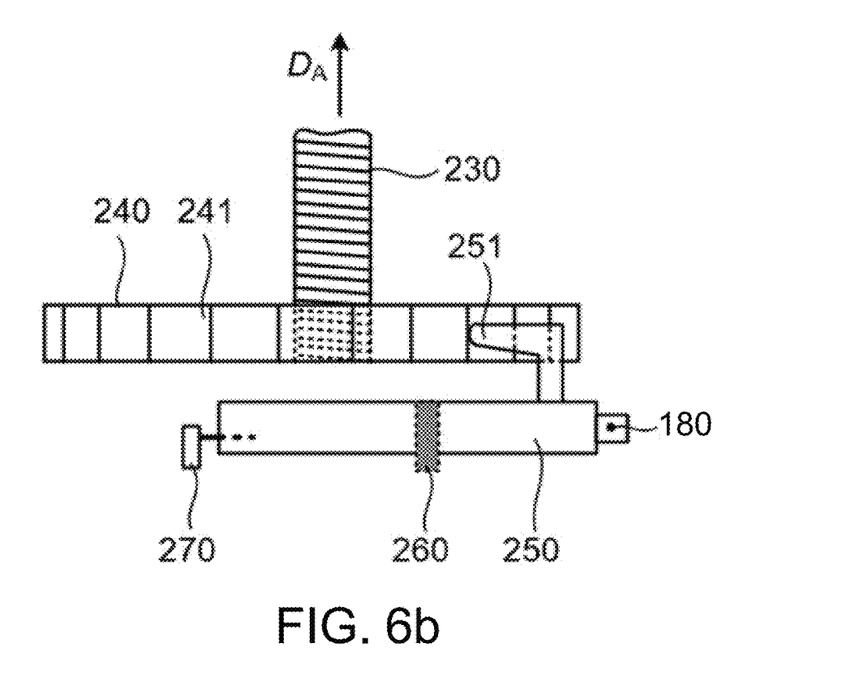

FIG. 6a-FIG. 6b are schematic structural diagrams of the driving portion 251 pushing the wheel teeth 241 to move according to the second embodiment of the present invention. The difference between the second embodiment and the first embodiment is that the direction of the power unit pulling force $F_P$ is perpendicular to the forward direction $D_A$ of the rigid screw 230 (in the second embodiment), and other structural designs are the same as those in the first embodiment.

FIG. 6a is a view along the axial direction of the rigid screw 230, and FIG. 6b is a schematic plan view of the structure of FIG. 6a. The rotating shaft 260 and the rebound unit 270 are provided on the base (not shown). As described above, the driving unit 250 rotating reciprocally in the R direction drives the driving portion 251 to push the wheel teeth 241, causing the driving wheel 240 to rotate in the W direction, and to drive the rigid screw 230 to advance in the $D_A$ direction. The driving principle of the driving unit 250 according to the embodiment of the present invention is consistent with the first embodiment, and details are not described herein again.

Figure 7:
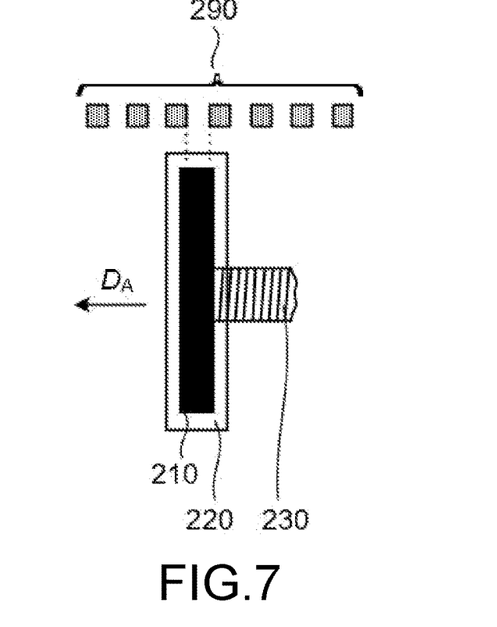
FIG. 7 is a schematic structural diagram of a piston and a position detector according to another embodiment of the present invention.

FIG. 7 is a schematic structural diagram of metal piece 210 and position detector 290 according to an embodiment of the present invention.

In the embodiment of the present invention, the rigid screw 230 is made of metallic material. The metal piece 210 is fixedly and electrically connected to the rigid screw 230. At a certain position, the metal piece 210 and a corresponding position detector 290 will form a capacitor to generate electrical signal(s). When the piston 220 moves, the capacitance changes with the area of the electrode plate, and the corresponding position detector 290 generates a changed electrical signal to accurately detect the position of the piston 220. The corresponding position detector 290 transmits the electrical signal to the program unit to be converted to the position information of the piston 220. And then the program unit outputs the remaining drug amount. Specifically, in the embodiment of the present invention, for accurate position detection, a plurality of position detectors 290 are provided, and the setting manner thereof is as described above.

The Third Embodiment

Figure 8:
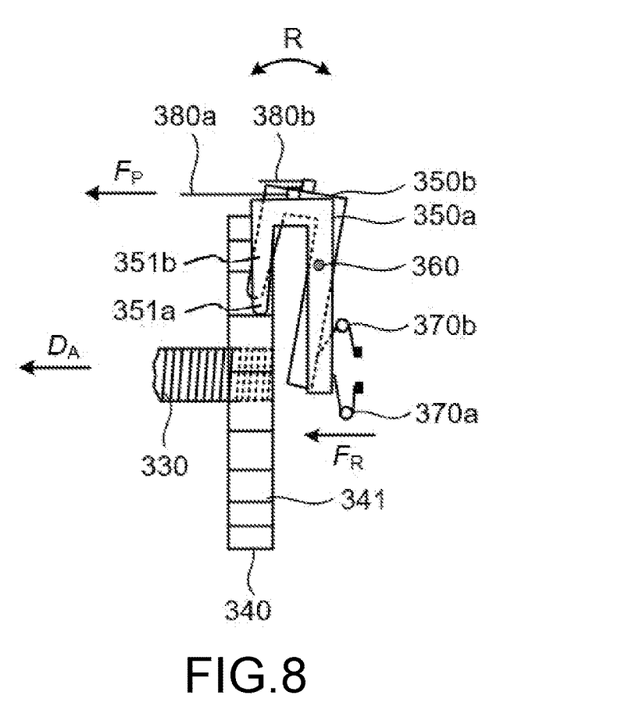
FIG. 8 is a schematic structural diagram of cooperation between a driving unit and a driving wheel according to another embodiment of the present invention.

FIG. 8 is a schematic structural diagram of the driving portion 351a or 351b pushing the wheel teeth 341 to move according to the third embodiment of the present invention. The difference from the previous embodiment is that two driving units 350a and 350b are provided which can rotate coaxially The driving unit 350a rotates reciprocally in the R direction around the rotating shaft 360 under the action of the power unit 380a and the rebound unit 370a. Similarly, the driving unit 350b rotates reciprocally in the R direction around the rotating shaft 360 under the action of the power unit 380b and the rebound unit 370b. In the embodiment of the present invention, the rotations of the two driving units do not interfere with each other.

Preferably, in the embodiment of the present invention, the driving unit 350a and the driving unit 350b rotate asynchronously. That is, when the driving portion 351a of the driving unit 350a pushes the wheel teeth 341 to move, the driving portion 351b of the driving unit 350b slides on the surface of the wheel teeth 341. When the driving portion 351b slides to the driving position of the next wheel tooth 341, the program unit controls the power unit 380a to stop outputting power to the driving unit 350a, and in turn controls the power unit 380b to output power to the driving unit 350b. At this time, the driving unit 350a rotates in the clockwise direction under the action of the rebound unit 370a, and the driving portion 351a slides on the surface of the wheel teeth, while the driving portion 351b pushes the wheel teeth 341. The driving units 350a and 350b are alternately powered to push the driving wheels 340.

In the embodiment of the present invention, the pulling force $F_P$ of the power units 380a and 380b, the elastic force $F_R$ of the rebound units 370a and 370b and the forward direction $D_A$ of the rigid screw 330 are shown in the figure. Like foresaid statement, the direction of the pulling force $F_P$ is parallel to the forward direction $D_A$ of the rigid screw 330.

The Fourth Embodiment

Figure 9:
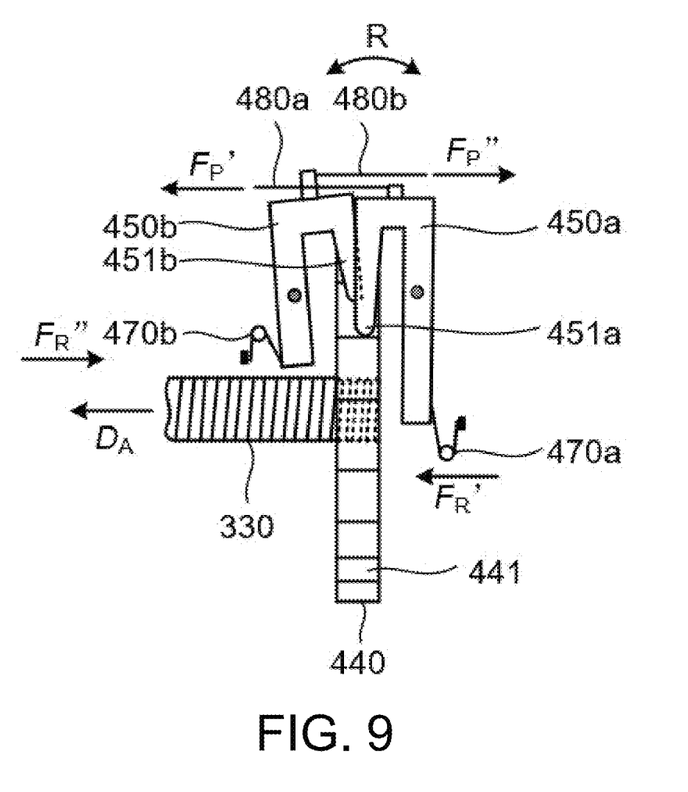
FIG. 9 is a schematic structural diagram of cooperation between a driving unit and a driving wheel according to another embodiment of the present invention.

FIG. 9 is a schematic structural diagram of a driving portion 451a or 451b pushing the wheel teeth 441 according to the fourth embodiment of the present invention. The fourth embodiment is different from the third embodiment in that the driving units 450a and 450b are respectively disposed on both sides of the driving wheel 440.

Similarly to the above, the driving portions 451a and 451b alternately push the wheel teeth 441, respectively, and the power output of the power units 480a and 480b are both controlled by the program unit.

It should be noted that, in the embodiment of the present invention, the direction of the pulling force $F_P'$ of the power unit 480a and the direction of the pulling force $F_P''$ of the power unit 480b are opposite. Obviously, the direction of the returning force $F_R'$ of the rebound unit 470a and the direction of the returning force $F_R''$ of the rebound unit 470b are also opposite.

Also, in the embodiment of the present invention, the driving units 450a and 450b rotate asynchronously. That is, when the driving portion 451a of the driving unit 450a pushes the wheel teeth 441 to move, the driving portion 451b of the driving unit 450b slides on the surface of the wheel teeth 441. When the driving portion 451b slides to the driving position of the next wheel tooth 441, the program unit controls the power unit 480a to stop outputting power to the driving unit 450a, and in turn controls the power unit 480b to output power to the driving unit 450b. The driving unit 450a returns to the clockwise rotation by the rebound unit 470a, while the driving portion 451a slides on the surface of the wheel teeth 441, and the driving portion 451b pushes the wheel teeth 441. The driving units 450a and 450b alternately pushes the driving wheels 440. Obviously, the direction of driving rotating or return rotating is opposite between the driving units 450a and 450b.

It should be noted that, in other embodiments of the present invention, more driving units or more driving wheels can be arranged. In this situation, different driving units respectively push the corresponding driving wheels to rotate. As in one embodiment of the present invention, the infusion device is provided with one driving unit and two driving wheels. The driving unit drives only one driving wheel, while the other driving wheel is used to balance the effect of force. In this case, the distance between the two driving wheels can be relatively short.

In the embodiment of the present invention, when two or more driving units are provided, by controlling the timing of different force output or by adjusting the distance between the front ends (as shown in FIG. 3) of multiple driving units, the infusion device can improve the infusion accuracy. As shown in FIG. 8 and FIG. 9, when the driving units are both at the end of the return rotating, the distance between the front ends of the two driving portions differs by n/2 (n is an odd number) tooth pitch. At this time, when the driving wheel rotates at most ½ tooth pitch, one driving unit will reach the next driving position leading to the next rotating. Compared to a single driving unit, the infusion increment (or the infusion unit amount) is halved. In the embodiment of the present invention, n=1, 3, or 5. In order to avoid possible interference between the two adjacent driving portions, it is preferable that n=3. Only rotating at most half a pitch at one time, the driving wheel can start the next rotation. The driving unit's rotation amplitude is further reduced, and the internal structure of the infusion device will be more compact and smaller.

In a kind of drug infusion device, one driving unit is provided with two driving portions, and the two driving portions are designed on both sides of the rotating shaft. At the same time, two driving wheels are required to cooperate with the two different driving units, in which way the width of the device's driving parts and the design complexity will be overall increased, resulting in increased device volume and production cost.

However, the driving unit of the infusion device in the embodiment of the present invention has only one driving portion, and the driving wheel is driven to rotate by reciprocal rotation of the driving unit similarly. Moreover, since there is only one driving portion, the rotating amplitude of the driving unit is reduced, and so is the width of it. The overall structure of the driving unit and the driving wheel is more compact, so that the space for structural assembly is reduced. Even if two driving wheels are provided, under the same conditions as mentioned above, the device structure of the embodiment of the present invention has a smaller width and a more compact structure, reducing the volume of the infusion device and the design and production costs.

In summary, the present invention discloses a patch-type drug infusion device. The driving unit is provided with one driving portion, which reduces the width and rotation amplitude of the driving unit, reducing the volume of the infusion device and the design and production costs.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A patch-type drug infusion device, comprising:
an infusion unit, the infusion unit including:
a drug storage unit, a piston and a rigid screw, wherein the piston is arranged in the drug storage unit and a metal piece is fixedly connected to the rigid screw and is arranged on the piston;
two rotating shafts, two rotatable driving units and one driving wheel provided with wheel teeth, wherein the driving units are respectively disposed on two sides of the driving wheel, each of the driving units includes one driving portion, and the driving units are able to respectively rotate around the rotating shafts, and respectively drive the driving portions to push the wheel teeth to rotate the driving wheel which engages the rigid screw to move forward in a non-rotating way; and
two power units and two rebound units, the power units and the two rebound units apply force to the driving units respectively to make the driving units rotate reciprocally;
a plurality of position detectors, wherein the metal piece and the plurality of position detectors interact to generate electrical signals or magnetic signals;
a program unit, wherein the program unit is connected to the infusion unit to control drug infusion and convert received electrical signals or magnetic signals into piston position information;
an infusion needle, wherein one end of the infusion needle is connected to an outlet of the drug storage unit, while the other end of the infusion needle pierces a skin to achieve drug infusion; and
an adhesive patch, wherein the adhesive patch is able to attach the infusion unit or the program unit to a skin surface.

2. The patch-type drug infusion device of claim 1, wherein
the rigid screw is a metal screw, and the metal piece is electrically connected with the metal screw, so that the metal piece and a corresponding position detector of the plurality of position detectors constitute a capacitor, and a linear movement of the metal piece causes a change in capacitance making the corresponding position detector of the plurality of position detectors generate an electrical signal.

3. The patch-type drug infusion device of claim 1, wherein the metal piece is a magnetic metal piece, and each position detector of the plurality of position detectors is a magnetic induction detector, a linear movement of the magnetic metal piece causes a change in a magnetic field around each position detector of the plurality of position detectors, and each position detector of the plurality of position detectors generates a magnetic signal.

4. The patch-type drug infusion device of claim 1, wherein
a direction in which the power units respectively apply a force to the driving units is parallel to a forward direction of the rigid screw.

5. The patch-type drug infusion device of claim 1, wherein
the infusion unit further includes a clutch structure movably disposed on the driving wheel, the rigid screw passes through the clutch structure, and the clutch structure is provided with an internal thread that cooperates with the rigid screw, the driving wheel drives the clutch structure to rotate, and with the internal thread engaging the rigid screw, the clutch structure drives the rigid screw to move forward in a non-rotating way.

6. The patch-type drug infusion device of claim 1, wherein
the infusion unit further includes a blocking wall, and the driving units stop rotating upon contacting the blocking wall.

* * * * *